US007718242B2

(12) United States Patent
Li et al.

(10) Patent No.: US 7,718,242 B2
(45) Date of Patent: *May 18, 2010

(54) ORGANIC DYES FOR RECORDING LAYER AND HIGH DENSITY OPTICAL RECORDING MEDIUM USING THE SAME

(75) Inventors: Ming-Chia Li, Taichung County (TW); Chien-Liang Huang, Taoyuan County (TW); An-Tze Lee, Taipei County (TW); Wen-Yih Liao, Taichung (TW); Ching-Yu Hsieh, Hsinchu County (TW); Tzuan-Ren Jeng, Hsinchu (TW)

(73) Assignee: Industrial Technology Research Institute, Hsinchu (TW)

( * ) Notice: Subject to any disclaimer, the term of this patent is extended or adjusted under 35 U.S.C. 154(b) by 495 days.
This patent is subject to a terminal disclaimer.

(21) Appl. No.: 11/672,378

(22) Filed: Feb. 7, 2007

(65) Prior Publication Data

US 2007/0160931 A1    Jul. 12, 2007

Related U.S. Application Data

(63) Continuation-in-part of application No. 11/330,387, filed on Jan. 10, 2006.

(51) Int. Cl.
*G11B 7/247* (2006.01)
*G11B 7/253* (2006.01)
*G11B 7/257* (2006.01)
*G11B 7/258* (2006.01)

(52) U.S. Cl. ............... 428/64.4; 428/64.7; 428/64.8; 428/64.9; 428/913; 430/270.18; 430/271.1; 430/273.1; 430/275.1; 430/277.1; 430/278.1; 430/945; 544/231; 544/296; 544/319; 544/333; 549/265; 549/274; 549/293; 549/333; G9B/7.152; G9B/7.175; G9B/7.189; G9B/7.19

(58) Field of Classification Search .......... 428/64.4, 428/64.7, 64.8, 64.9, 65.1, 913; 430/270.18, 430/271.1, 272.1, 273.1, 275.1, 277.1, 278.1, 430/945; 544/231, 296, 319, 333; 549/265, 549/333, 274, 333; G9B/7.152, 7.189, 1.19
See application file for complete search history.

(56) References Cited

U.S. PATENT DOCUMENTS 3,440,052 A * 4/1969 Heseltine .................. 430/578

(Continued)

FOREIGN PATENT DOCUMENTS

WO    WO 2004086390 A1 * 10/2004

OTHER PUBLICATIONS

STN search for compounds having a more complete dimer structure. Performed on Jul. 13, 2009. See STN1.*

(Continued)

*Primary Examiner*—Mark Ruthkosky
*Assistant Examiner*—Gerard T Higgins
(74) *Attorney, Agent, or Firm*—J.C. Patents (57) ABSTRACT

A recording layer including a novel dye for a high density optical recording medium, employing short wavelength laser source with a wavelength not longer than 530 nm for recording high density information and reproduction/playback of the high density information recordings, is provided. The dye incorporated in the recording layer has the following general chemical structural formula (III):

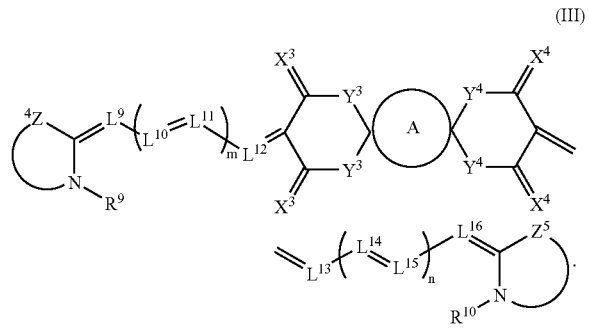

11 Claims, 4 Drawing Sheets

U.S. PATENT DOCUMENTS

| | | | |
|---|---|---|---|
| 3,637,676 A * | 1/1972 | Heseltine | 548/150 |
| 3,844,798 A * | 10/1974 | Ohlschlager et al. | 430/578 |
| 2004/0166441 A1* | 8/2004 | Akiba et al. | 430/270.18 |
| 2007/0042295 A1* | 2/2007 | Berneth et al. | 430/270.14 |
| 2007/0085074 A1* | 4/2007 | Wang et al. | 257/40 |
| 2007/0105049 A1* | 5/2007 | Lee et al. | 430/270.18 |

OTHER PUBLICATIONS

STN search for compounds having a broader structure. Performed on Jul. 13, 2009. See STN2.*

* cited by examiner

ORGANIC DYES FOR RECORDING LAYER AND HIGH DENSITY OPTICAL RECORDING MEDIUM USING THE SAME

CROSS-REFERENCE TO RELATED APPLICATION

This application is a continuation-in-part of a prior application Ser. No. 11/330,387, filed Jan. 10, 2006, all disclosures are incorporated therewith.

BACKGROUND OF THE INVENTION

1. Field of the Invention

The present invention generally relates to a high density optical recording medium. More particularly, the present invention relates to a high density optical recording medium employing short wavelength laser that makes high density storage and reproduction/playback of the high density information records possible.

2. Description of Related Art

In recent years, development of optical recording media employing laser have been remarkable. An example of the optical recording medium, such as an optical disc, is generally designed to irradiate a focused laser beam of about 1 μm to a thin recording layer formed on a disc shaped substrate to conduct information recording. The recording is implemented in a manner that upon absorption of the laser beam energy, the irradiated portion of the recording layer undergoes a thermal deformation such as decomposition, evaporation or melting. Reproduction of the recorded information is carried out by reading the difference in the reflectance between the portion having a deformation formed by the laser beam and the portion without such deformation.

Accordingly, an optical recording medium is required to efficiently absorb the energy of the laser beam, and is also required to have a predetermined amount of absorbed light to a laser beam having a specific wavelength employed for recording and to be high in the reflectance to laser beam having a specific wavelength employed for reproduction for accurately conducting the reproduction of information.

However, storage capacity of the optical recording medium employing the laser source is limited due to optical diffraction. At present, some principles and methods of enhancement of the storage density of the optical information storage media are being set forth, including such as shifting of the wavelength of the laser source, for example, from red laser to blue laser, or enhancement of the objective numerical aperture ("NA") of optical lens. Some other methods include improvement of the encoding methods of the digital signal, or a disc storage method using an extra-fine resolution near field optical structure, or a technology for increasing the storage capacity of the information storage media (e.g., a compact disc) by using stacked multiple recording layers, i.e., the recording layers of the information storage media is developed into a three dimensional space multilayer structure, to increase the storage capacity. All the methods described above may be employed to effectively increase the storage capacity of the optical recording medium.

In the method of the shifting to shorter wavelength laser source, a new generation of a high density disc storage specification (BLU-RAY DISC™) is published in 2002 by companies such as Hitachi, LG, National, Pioneer, Philips, Samsung, Sharp, Sony and Thomson Multimedia in common. A single-side BLU-RAY DISC™ may be promoted up to 27 GB by employing a 405 nm blue laser source and a 0.1 mm optical transmission cover layer structure. Thus, optical recording medium employing a short wavelength laser source for reading and storage operations has become the main stream of the development of the high density optical recording media.

SUMMARY OF THE INVENTION

Accordingly, the present invention is directed to a high density optical recording medium employing short wavelength laser source with a wavelength no longer than 530 nm for recording high density information and reproduction/playback of the high density information recordings.

The present invention provides dyes for a recording layer suitable for an optical recording medium employing short wavelength laser source with a wavelength no longer than 530 nm for recording high density information and reproduction/playback of the high density information recordings.

According to an aspect of the present invention, the dyes mentioned above shows absorption at wavelength within a range of 300 to 600 nm, and is excellent in the light fastness and thermal stability.

The dye of the present invention mentioned above has a following general chemical structural formula:

(I)

wherein n is an integer of 0 or 1, $X^1$ represents oxygen atom or $C(CN)_2$, $Y^1$ represents oxygen atom, $CH_2$, or $N-R^{11}$, $L^1$, $L^2$, $L^3$, $L^4$ represent substituted or non-substituted methine group, $R^1$ represents substituted or non-substituted alkyl group with carbon number 1-18 ($C_{1-18}$), substituted or non-substituted alkoxy group with carbon number 1-18 ($C_{1-18}$), substituted or non-substituted carboxyl group with carbon number 1-18 ($C_{1-18}$), substituted or non-substituted alkyl ester group with carbon number 1-18 ($C_{1-18}$), substituted or non-substituted arylester, adamantyl carbonyl group, adamantyl group, substituted or non-substituted aralkyl group, $R^2$ and $R^3$ represent hydrogen atom, substituted or non-substituted alkyl group, substituted or non-substituted aryl group, substituted or non-substituted aralkyl group, substituted or non-substituted heterocyclic ring, ferrocenyl group, $R^{11}$ represents substituted or non-substituted alkyl group with carbon number 1-18 ($C_{1-18}$), $Z^1$ represents substituted or non-substituted alkylene group, oxygen atom, sulfur atom, selenium atom or nitrogen atom, so as to form a heterocyclic structure.

(II)

wherein k is an integer of 0 or 1, $X^2$ represents oxygen atom or $C(CN)_2$, $Y^2$ represents oxygen atom, $CH_2$, or $N-R^{11}$, $L^5$, $L^6$, $L^7$, $L^8$ represent substituted or non-substituted methine group, $R^4$ represents substituted or non-substituted alkyl group with carbon number 1-18 ($C_{1-18}$), substituted or non-substituted alkoxy group with carbon number 1-18 ($C_{1-18}$), substituted or non-substituted carboxyl group with carbon number 1-18 ($C_{1-18}$), substituted or non-substituted alkyl ester group with carbon number 1-18 ($C_{1-18}$), substituted or non-substituted arylester, adamantyl carbonyl group, adamantyl group, substituted or non-substituted aralkyl group, $R^6$, $R^7$, $R^8$ represent hydrogen atom, substituted or non-substituted alkyl group, substituted or non-substituted aryl group, substituted or non-substituted aralkyl group, substituted or non-substituted heterocyclic ring, $R^{11}$ represents substituted or non-substituted alkyl group with carbon number 1-18 ($C_{1-18}$), $Z^2$, $Z^3$ individually represents substituted or non-substituted alkylene group, oxygen atom, sulfur atom, selenium atom, or nitrogen atom, so as to form a heterocyclic structure.

DESCRIPTION OF THE INVENTION

It is to be understood that both the foregoing general description and the following detailed description are exemplary, and are intended to provide further explanation of the invention as claimed.

The present invention provides a dye suitable for a recording layer for fabricating a high density optical recording medium employing short wavelength laser source with a wavelength not longer than 530 nm for recording high density information and reproduction/playback of the high density information recordings. The dye has the following general chemical structural formula:

(III)

(I)

wherein m is an integer of 0 or 1, A represents substituted or non-substituted cyclic alkyl group, $X^3$, $X^4$ represents oxygen atom or $C(CN)_2$, $Y^3$, $Y^4$ represents oxygen atom, $CH_2$, or $N-R^{11}$, $L^9$, $L^{10}$, $L^{11}$, $L^{12}$, $L^{13}$, $L^{14}$, $L^{15}$ and $L^{16}$ represent substituted or non-substituted methine group, $R^9$, $R^{10}$ represent substituted or non-substituted alkyl group with carbon number 1-18 ($C_{1-18}$), substituted or non-substituted alkoxy group with carbon number 1-18 ($C_{1-18}$), substituted or non-substituted carboxyl group with carbon number 1-18 ($C_{1-18}$), substituted or non-substituted alkyl ester group with carbon number 1-18 ($C_{1-18}$), substituted or non-substituted arylester, adamantyl carbonyl group, adamantyl group, substituted or non-substituted aralkyl group, $R^{11}$ represents substituted or non-substituted alkyl group with carbon number 1-18 ($C_{1-18}$), $Z^4$ and $Z^5$ represent substituted or non-substituted alkylene group, oxygen atom, sulfur atom, selenium atom or nitrogen atom, so as to form a heterocyclic structure.

The dyes of the present invention can be employed for, for example, a recording layer of an optical recording medium. Because the dyes of the present invention shows absorption at a wavelength ranging from 300 nm to 600 nm, it is possible to fabricate a high density optical recording medium employing a short wavelength laser source with a wavelength no longer than 530 nm, preferably a laser source with a wavelength of 405 nm, for recording high density information and reproduction/playback of the high density information recordings.

BRIEF DESCRIPTION OF THE DRAWINGS

The accompanying drawings are included to provide a further understanding of the invention, and are incorporated in and constitute a part of this specification. The drawings illustrate embodiments of the invention, and together with the description, serve to explain the principles of the invention.

wherein n is an integer of 0 or 1, $X^1$ represents oxygen atom or $C(CN)_2$, $Y^1$ represents oxygen atom, $CH_2$, or $N-R^{11}$, $L^1$, $L^2$, $L^3$, $L^4$ represent substituted or non-substituted methine group, $R^1$ represents substituted or non-substituted alkyl group with carbon number 1-18 ($C_{1-18}$), substituted or non-substituted alkoxy group with carbon number 1-18 ($C_{1-18}$), substituted or non-substituted carboxyl group with carbon number 1-18 ($C_{1-18}$), substituted or non-substituted alkyl ester group with carbon number 1-18 ($C_{1-18}$), substituted or non-substituted arylester, adamantyl carbonyl group, adamantyl group, substituted or non-substituted aralkyl group, $R^2$ and $R^3$ represent hydrogen atom, substituted or non-substituted alkyl group, substituted or non-substituted aryl group, substituted or non-substituted aralkyl group, substi tuted or non-substituted heterocyclic ring, ferrocenyl group, $R^{11}$ represents substituted or non-substituted alkyl group with carbon number 1-18 ($C_{1-18}$), $Z^1$ represents substituted or non-substituted alkylene group, oxygen atom, sulfur atom, selenium atom or nitrogen atom, so as to form a heterocyclic structure.

tuted or non-substituted heterocyclic ring, $R^{11}$ represents substituted or non-substituted alkyl group with carbon number 1-18 ($C_{1-18}$), $Z^2$, $Z^3$ individually represents substituted or non-substituted alkylene group, oxygen atom, sulfur atom, selenium atom, or nitrogen atom, so as to form a heterocyclic structure.

(III)

(II)

wherein k is an integer of 0 or 1, $X^2$ represents oxygen atom or $C(CN)_2$, $Y^2$ represents oxygen atom, $CH_2$, or N—$R^{11}$, $L^5$, $L^6$, $L^7$, $L^8$ represent substituted or non-substituted methine group, $R^4$ represents substituted or non-substituted alkyl group with carbon number 1-18 ($C_{1-18}$), substituted or non-substituted alkoxy group with carbon number 1-18 ($C_{1-18}$), substituted or non-substituted carboxyl group with carbon number 1-18 ($C_{1-18}$), substituted or non-substituted alkyl ester group with carbon number 1-18 ($C_{1-18}$), substituted or non-substituted arylester, adamantyl carbonyl group, adamantyl group, substituted or non-substituted aralkyl group, $R^5$, $R^6$, $R^7$, $R^8$ represent hydrogen atom, substituted or non-substituted alkyl group, substituted or non-substituted aryl group, substituted or non-substituted aralkyl group, substi- wherein m is an integer of 0 or 1, A represents substituted or non-substituted cyclic alkyl group, $X^3$, $X^4$ represents oxygen atom or $C(CN)_2$, $Y^3$, $Y^4$ represents oxygen atom, $CH_2$, or N—$R^{11}$, $L^9$, $L^{10}$, $L^{11}$, $L^{12}$, $L^{13}$, $L^{14}$, $L^{15}$ and $L^{16}$ represent substituted or non-substituted methine group, $R^9$, $R^{10}$ represent substituted or non-substituted alkyl group with carbon number 1-18 ($C_{1-18}$), substituted or non-substituted alkoxy group with carbon number 1-18 ($C_{1-18}$), substituted or non-substituted carboxyl group with carbon number 1-18 ($C_{1-18}$), substituted or non-substituted alkyl ester group with carbon number 1-18 ($C_{1-18}$), substituted or non-substituted arylester, adamantyl carbonyl group, adamantyl group, substituted or non-substituted aralkyl group, $R^{11}$ represents substituted or non-substituted alkyl group with carbon number 1-18 ($C_{1-18}$), $Z^4$ and $Z^5$ represent substituted or non-substituted alkylene group, oxygen atom, sulfur atom, selenium atom or nitrogen atom, so as to form a heterocyclic structure.

The dyes (I), (II) and (III) of the present invention show absorption in wavelength range of 300 to 600 nm and are excellent in the light fastness and thermal stability. Therefore, it is possible to produce a high density optical medium by employing the recording layer incorporated with the dye of the present invention so that a short wavelength laser having a wavelength no longer than 530 nm, preferably a blue laser with a wavelength 405 nm, may be employed for recording high density information on the recording layer and reproduction/playback of the same.

Following are some of the specific derivatives of the dye (I), (II), (III) of the present invention. However, the scope of the present invention is not limited to the listed examples hereafter.

(1)

(2)

(3)

(4)

(5)

-continued (7)

(8)

(9)

(10)

(11)

(12)

(13)

-continued (14)

(16)

(17)

(18)

(19)

(20)

Figure 1:
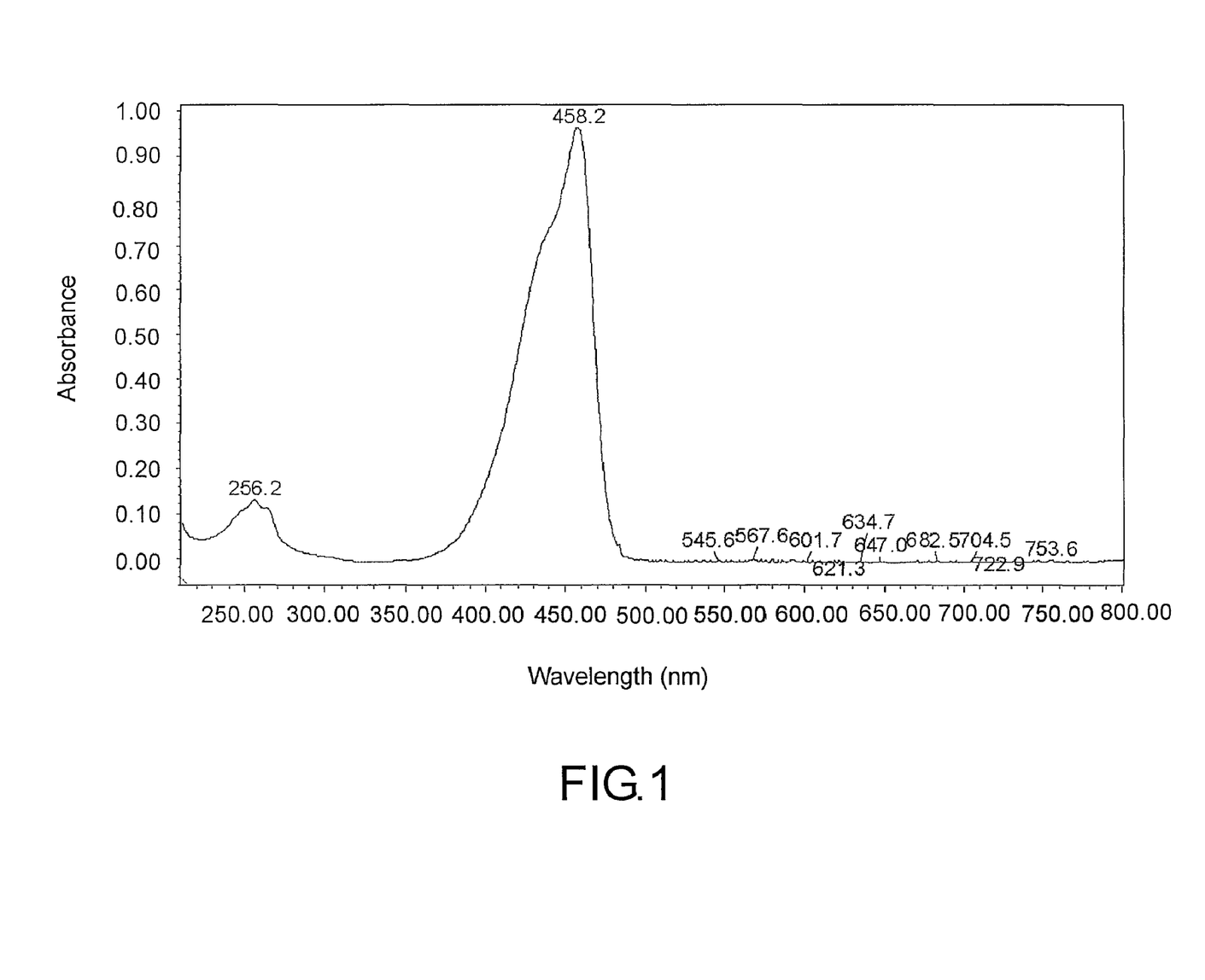
FIG. 1 illustrates an UV/Visible/IR absorption spectrum of the dye derivative (2) of the present invention.

FIG. 1 illustrates an UV/Visible/IR absorption spectrum of the dye derivative (2) of the present invention.

Figure 2:
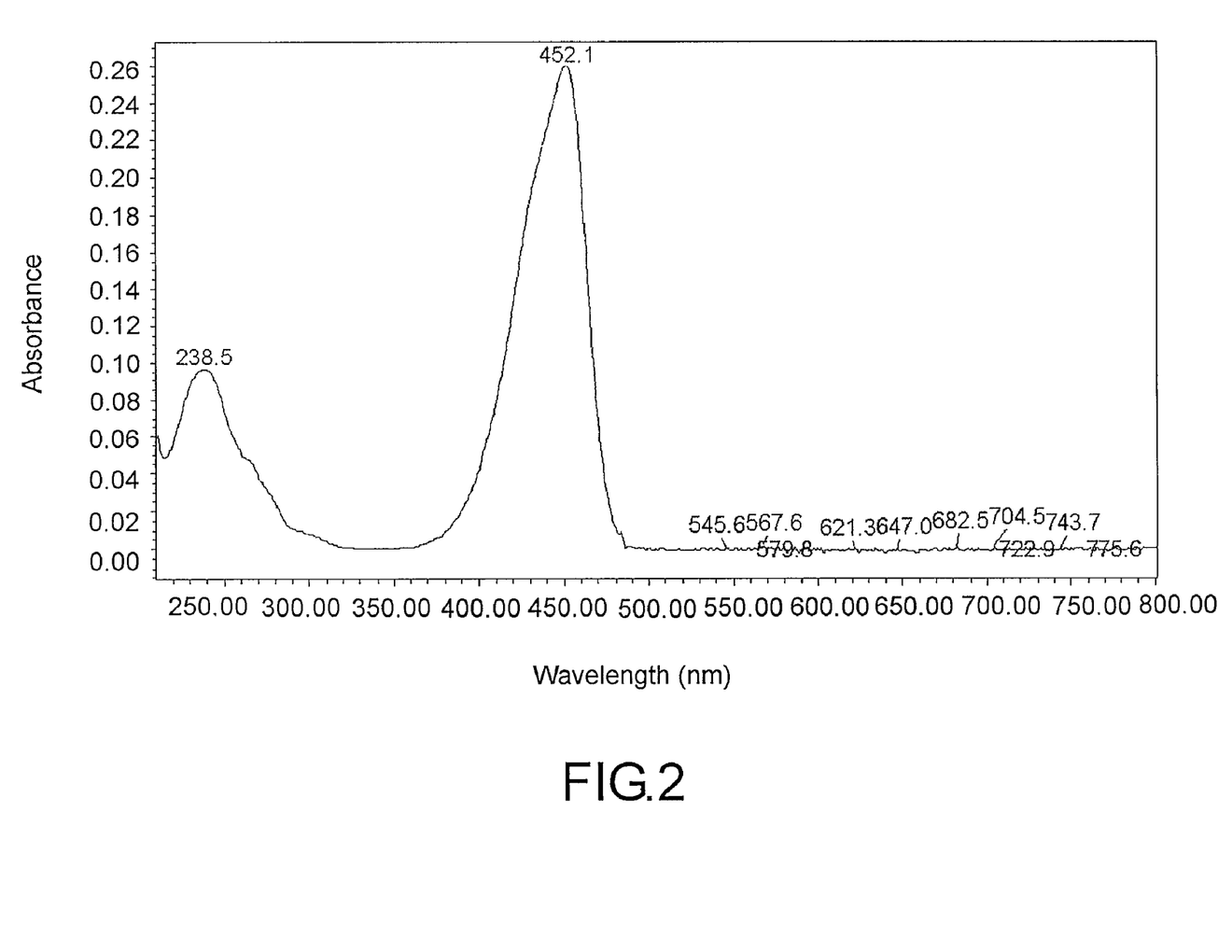
FIG. 2 illustrates an UV/Visible/IR absorption spectrum of the dye derivative (5) of the present invention.

FIG. 2 illustrates an UV/Visible/IR absorption spectrum of the dye derivative (5) of the present invention.

Herein, the synthesis process for the dye derivative (7) is described as an example, and the reaction scheme is as follows:

According to the above reaction scheme, the synthesis process may be described as follows. First, 0.1 mole of Compound A and 0.1 mole N,N'-diphenylformamidine are added to the methanol solution containing 0.12 mole triethylamine, and then the mixture is heated to the reflux temperature. The reaction mixture is maintained at this condition for 8 hours. Once the reaction is complete, the resulting mixture is allowed to settle overnight. Thereafter, the precipitate is filtered and collected to obtain the intermediate Compound B.

Next, 0.1 mole of Compound B and 0.12 mole 2-methyl-2-phenyl-1,3-dioxane-4,6-dione are added to the diethylformamide (DEF) solution containing 0.12 mole triethylamine, and then the mixture is heated up to 100° C. and the mixture is allowed to react for 8 hours. Once the reaction is complete, the mixture is allowed to settle overnight. Next, the precipitates were filtered and collected to obtain the derivative compound (7).

Those skilled in the art would understand that the dyes and their derivatives may be synthesized through various chemical reactions and under different reaction schemes, the above reaction scheme is merely an example and the steps and conditions for the synthesis processes for all the compounds within the scope of this invention will not be described in details herein.

Figure 3:
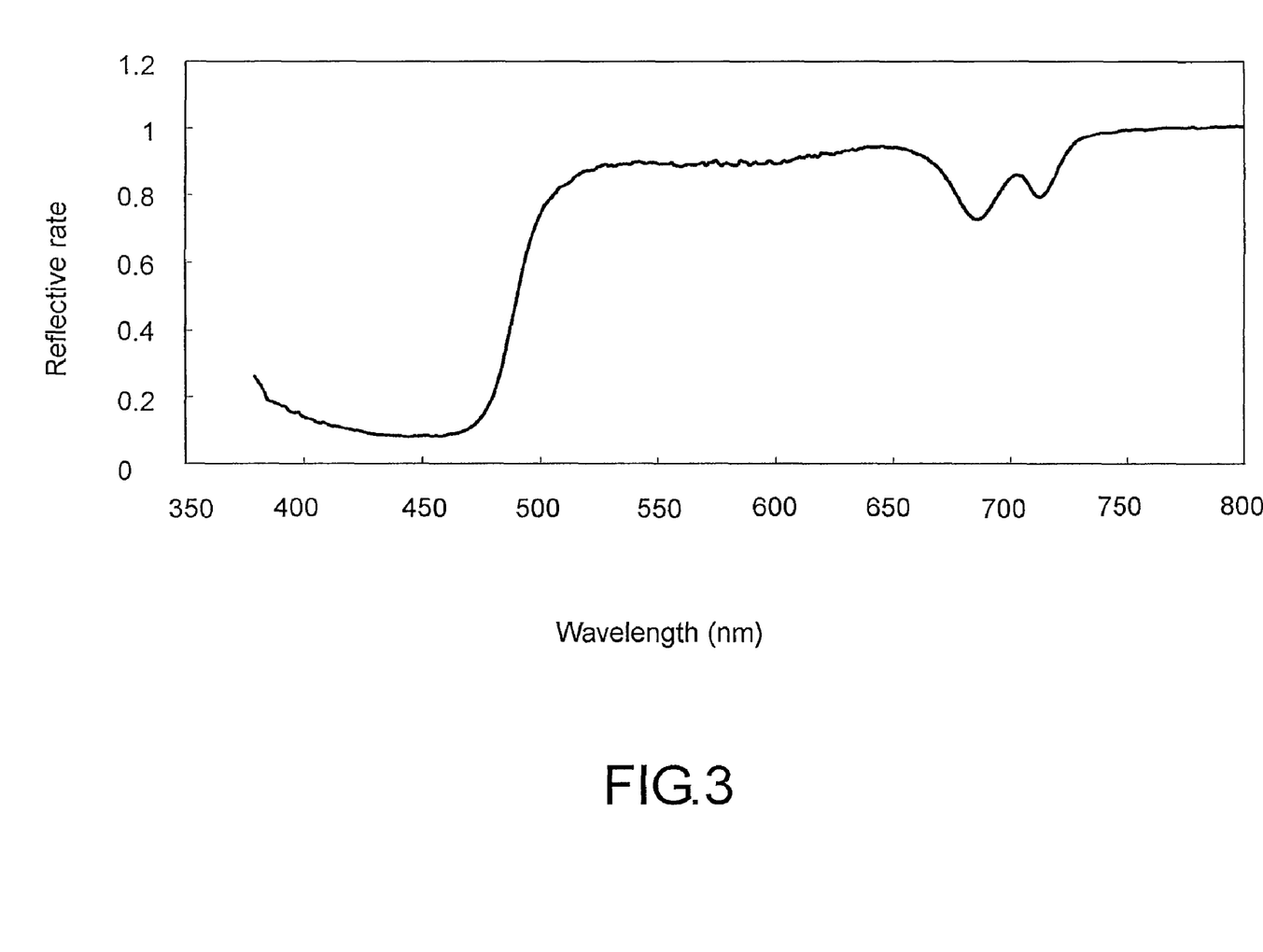
FIG. 3 illustrates a reflective spectrum for the disc having a HD-DVD-R recording layer of the dye derivative (2) of the present invention.

FIG. 3 illustrates a reflective spectrum for the disc having a HD-DVD-R recording layer of the dye derivative (2) of the present invention.

Figure 4:
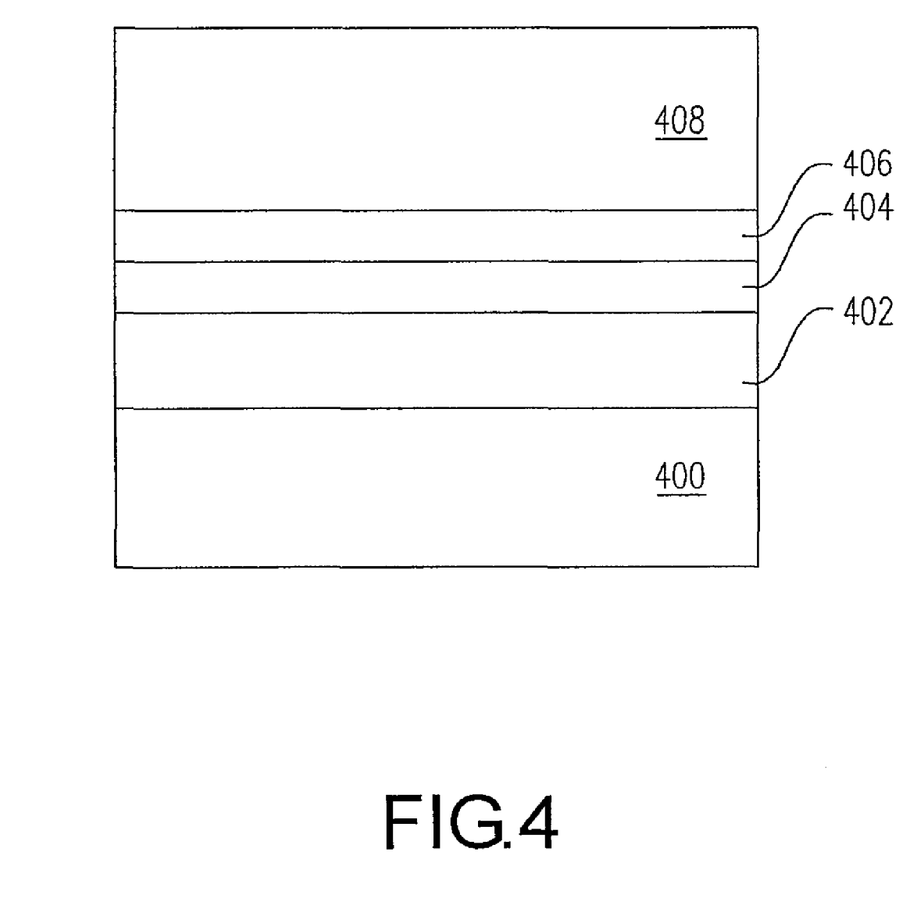
FIG. 4 illustrates cross sectional view of a high density optical recording medium according to an embodiment of the present invention.

Hereinafter, a structure of a blue-ray high density optical recording medium will be described with reference to FIG. 4 as follows. Referring to FIG. 4, the high density optical recording medium comprises a first substrate 400, a cover layer 408 and at least a recording layer 402, containing at least one of the derivatives of the dye (I), (II), (III) of the present invention described above, disposed between the first substrate 400 and the cover layer 408. Furthermore, a reflective layer 406 may be provided on the recording layer 402 and also, if necessary, a primer coating layer may be provided on the first substrate 400, a protective layer 404 may be provided on the recording layer 402 or the reflective layer 406, and a surface protective layer may be provided on the first substrate 400 at the opposite side to the recording layer 402.

According to an aspect of the present invention, the first substrate 400 and the cover layer 408 are preferably transparent to the laser beam. The material of the first substrate 400 and the cover layer 408 may be comprised of, for example but not limited to, glass or plastic materials. From various aspects, the plastic material is preferably used. The plastic material may be comprised of, for example but not limited to, polycarbonate (PC), polymethylmethacrylate (PMMA), polymer resins, glass, acryl resin, methacryl resin, vinyl acetate resin, vinyl chloride resin, nitro cellulose, polyethylene resin, polypropylene resin, polycarbonate resin, polyimide resin, epoxy resin, polysulfone resin and metallocene based cyclic olefin copolymer (mCOC). Among the plastic materials mentioned above, an injection molded polycarbonate resin substrate may of particular interest from the viewpoint of the high productivity, low cost and moisture resistance. The thickness of the first substrate 400 may be between 0.5 mm to 1.3 mm, more preferably about 0.6 mm. The first substrate 400, for example, comprises lands, or pre-curved pits or grooves with a track pitch of less than 0.4 μm. The lands, or pre-curved pits or grooves in the first substrate 400 are used to provide a signal surface for the laser tracking of the pick-up head of the laser.

According to an aspect of the present invention, the recording layer 402 of the present invention containing the dye (I), (II) or (III) is formed with a thickness in a range of about 10 Å to 500 nm, preferably in a range of about 5 nm to 200 nm. The recording layer 402 of the present invention may be formed by employing well known thin-film-forming methods such as a spin coating method, a roller press method, a vacuum vapor deposition method, a sputtering method, a doctor blade method, a casting method, inkjet printing method or a dipping method. However, the spin coating method is preferred from the viewpoint of the productivity and cost. A 1.5 Wt. % solution of the dye (I), (II), (III) of the present invention in 2,2,3,3-tetrafluoropropanol may be prepared and used for spin coating the thin film recording layer 402 over the first substrate 400. It should also be noted that other solvents such as alcohol, ketone, ether, chloroform or dichloromethane may also be used to make the dye solution for forming the thin film recording layer 402. Preferred examples of alcohol include 2,2,3,3-tetrafluoropropanol, methanol, ethanol and isopropanol. Preferred examples of ketone include acetone and dimethyl-ethyl ketone. Preferred examples of ether include ethyl ether and tetrahydrofuran.

According to an aspect of the present invention, the reflective layer 406 may be comprised of, for example but not limited to, metals such as gold, silver, copper, aluminum or platinum, titanium and alloys thereof, or equivalents thereof, which have high reflectance in the laser wavelength region to be employed. The thickness of the reflective layer 406 may be about 1 nm to 300 nm. The reflective layer 406 may be formed on the recording layer 402 using vacuum sputtering.

Finally, the cover layer 408 may be adhered over the reflective layer 406 to complete the fabrication of the blue-ray high density optical recording medium. The cover layer 408 may be adhered over the reflective layer 406 by spin coating, screen printing, thermal gluing or roller pressing.

According to an aspect of the present invention, the surface protective layer on the mirror surface side of the first substrate may be comprised of, for example but not limited to, an ultraviolet curable acryl resin or a silicon type hard coating agent. The surface protective is preferably provided with an antistatic ability for preventing dust or the like from adhering.

The recording layer 402 of the optical recording medium of the present invention may be formed on one side of the first substrate 400. According to an aspect of the present invention, multiple recording layers may be used for fabricating a multi-layer stacked optical recording medium structure with a view of further increasing the storage capacity of the optical recording medium.

Recording on an optical recording medium thus obtained, may be conducted by irradiating a laser beam with a wavelength no longer than 530 nm, for example using a blue laser with a wavelength of 405 nm, to the recording layer. At the portion irradiated with the laser beam, a thermal deformation of the recording layer, such as decomposition, evaluation or melting may be formed due to absorption of the laser energy. Reproduction of the recorded information can be conducted by reading the difference in the reflectance between the portion having such a thermal deformation formed by a laser beam and the portion having no such a thermal deformation.

The recording and reproduction characteristics of the above optical recording medium was evaluated using a PULSTEC ODU-1000 instrument under the conditions including a blue laser beam with wavelength of 405 nm, objective lens numerical aperture (NA) of 0.65, CLV=6.61 m/s, reflective layer (Ag)=150 nm; Type 1: High to low, reference (16%~32%); Type 2: Low to high, reference (14%~28%), and recording pattern 3T, 11T. The recording efficiency was found to be in a range of 7 to 12 mW and the reading efficiency was found to be 0.5 mW. As can be seen from the recording and reproduction characteristics results shown in table 1 below that the optical recording medium incorporating the recording layer including the dye derivatives (2 and 5) of the present invention maintained recording and reading efficiencies below 10 mW and the CNR of both recording pattern maintained a high level, for example between 45-48 dB. Thus, the organic dye derivatives of the present invention described above can be practically used as an optical recording material for a recording layer for, for example, a blue-ray HD-DVD-R.

TABLE 1

| DYE | Max Abs. (MeOH)/nm | n + ik (405 nm) | Writing Power | 3TCNR | PRSNR | SbER |
|---|---|---|---|---|---|---|
| Dye (2) | 458 nm | 1.023 + 0.448i | 8.5 mW | 45 dB | 24 | 2.4*10 − 6 |
| Dye (5) | 452 nm | 1.118 + 0.331i | 7.5 mW | 48 dB | 19 | 7.6*10 − 6 |

Wherein n represents the actual refractive index of the dye film, k represents the imaginary of the refraction for the dye film, CNR represents Carrier-to-Noise Ratio, PRSNR represents Partial Response Signal-to-Noise Ratio and SbER represents Simulated bit Error Rate.

Since the recording layer incorporated with the dye (I), (II), (III) of the present invention shows absorption in the range of 300 to 600 nm and is excellent in the light fastness and thermal stability, it is possible employ a short wavelength laser with a wavelength no longer than 530 nm, preferably a blue laser with a wavelength of about 405 nm, to record high density information thereon and reproduce the high density information recorded thereon. Thus, the recording layer incorporated with the dye (I), (II), (III) of the present invention makes fabrication of a high density optical recording medium possible.

It will be apparent to those skilled in the art that various modifications and variations can be made to the structure of the present invention without departing from the scope or spirit of the invention. In view of the foregoing, it is intended that the present invention covers modifications and variations of this invention provided they fall within the scope of the following claims and their equivalents.

What is claimed is:

1. An organic compound having a following general chemical structural formula:

(III)

wherein m is an integer of 0 or 1, A represents substituted or non-substituted cyclic alkyl group, $X^3$, $X^4$ represents oxygen atom or $C(CN)_2$, $Y^3$, $Y^4$ represents oxygen atom, $CH_2$, or $N-R^{11}$, $L^9$, $L^{10}$, $L^{11}$, $L^{12}$, $L^{13}$, $L^{14}$, $L^{15}$ and $L^{16}$ represent substituted or non-substituted methine group, $R^9$, $R^{10}$ individually represents substituted or non-substituted alkyl group with carbon number 1-18 ($C_{1-18}$), substituted or non-substituted alkoxy group with carbon number 1-18 ($C_{1-18}$), substituted or non-substituted carboxyl group with carbon number 1-18 ($C_{1-18}$), substituted or non-substituted alkyl ester group with carbon number 1-18 ($C_{1-18}$), substituted or non-substituted arylester, adamantyl carbonyl group, adamantyl group, substituted or non-substituted aralkyl group, $R^{11}$ represents substituted or non-substituted alkyl group with carbon number 1-18 ($C_{1-18}$), $Z^4$, $Z^5$ individually represents substituted or non-substituted alkylene group, oxygen atom, sulfur atom, selenium atom, or nitrogen atom, so as to form a heterocyclic structure.

2. A high-density optical recording medium, employing a short-wavelength laser with a wavelength not longer than 530 nm for data reading and recording, comprising: a first substrate and a cover layer; and at least a recording layer, disposed between the first substrate and the cover layer, wherein the recording layer comprises at least an organic compound as recited in claim 1.

3. The high-density optical recording medium of claim 2, wherein a material of the first substrate and the cover layer is selected from the group consisting of polycarbonate (PC), polymethylmethacrylate (PMMA), polymer resins, glass, acryl resin, methacryl resin, vinyl acetate resin, vinyl chloride resin, nitro cellulose, polyethylene resin, polypropylene resin, polycarbonate resin, polyimide resin, epoxy resin, polysulfone resin and metallocene based cyclic olefin copolymer (mCOC).

4. The high-density optical recording medium of claim 2, wherein a thickness of the first substrate is between 0.5 mm to 1.3 mm.

5. The high-density optical recording medium of claim 2, wherein a thickness of the cover layer is between 0.01 mm to 0.7 mm.

6. The high-density optical recording medium of claim 2, wherein the first substrate comprises a land-and-groove surface on a single side thereof.

7. The high-density optical recording medium of claim 2, further comprising a reflective layer disposed between the cover layer and the first substrate and a material of the reflective layer is selected from the group consisting of gold, silver, copper, aluminum, platinum, titanium and alloys thereof.

8. The high-density optical recording medium of claim 7, further comprising a protective layer disposed on the recording layer or the reflective layer.

9. The high-density optical recording medium of claim 8, wherein a material of the protective layer comprises SiN, $SiO_2$, ZnS—$SiO_2$, or an ultraviolet curable acryl resin.

10. The high-density optical recording medium of claim 2, wherein a method for forming the recording layer is selected from the group consisting of a spin coating method, a roller press method, inkjet printing method and a dipping method.

11. The high-density optical recording medium of claim 7, wherein a method for adhering the cover layer to the reflective layer is selected from the group consisting of a spin coating method, a screen printing method and a thermal glue method.

* * * * *